(12) United States Patent
Engwall et al.

(10) Patent No.: US 11,565,127 B2
(45) Date of Patent: Jan. 31, 2023

(54) SYSTEM AND METHOD FOR DETERMINING A TREATMENT PLAN FOR ACTIVE ION BEAM TREATMENT

(71) Applicant: RaySearch Laboratories AB, Stockholm (SE)

(72) Inventors: Erik Engwall, Hägersten (SE); Martin Janson, Enskededalen (SE); Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/471,055

(22) PCT Filed: Dec. 20, 2017

(86) PCT No.: PCT/EP2017/083736
§ 371 (c)(1),
(2) Date: Jun. 19, 2019

(87) PCT Pub. No.: WO2018/115079
PCT Pub. Date: Jun. 28, 2018

(65) Prior Publication Data
US 2019/0344097 A1    Nov. 14, 2019

(30) Foreign Application Priority Data
Dec. 21, 2016   (EP) ..................................... 16205627

(51) Int. Cl.
*A61N 5/10*   (2006.01)
*G16H 20/40*  (2018.01)

(52) U.S. Cl.
CPC ......... *A61N 5/1031* (2013.01); *A61N 5/1043* (2013.01); *A61N 2005/1087* (2013.01); *G16H 20/40* (2018.01)

(58) Field of Classification Search
None
See application file for complete search history.

(56) References Cited

U.S. PATENT DOCUMENTS

| 3,634,684 | A  | * | 1/1972  | Sato ....................... H01J 37/09 313/313 |
| 6,511,575 | B1 | * | 1/2003  | Shindo .................. B08B 7/0035 257/E21.582 |
| 9,661,736 | B2 | * | 5/2017  | O'Neal, III ............ H05H 13/02 |
| 9,681,531 | B2 | * | 6/2017  | Gall ...................... A61N 5/1065 |
| 2007/0252093 | A1 | * | 11/2007 | Fujimaki .................. G21K 5/04 250/492.3 |
| 2008/0023644 | A1 | * | 1/2008  | Pedroni ................ A61N 5/1043 250/396 ML |

(Continued)

FOREIGN PATENT DOCUMENTS

| CN | 102214494 A | 10/2011 |
| EP | 2 952 225 A1 | 12/2015 |

(Continued)

*Primary Examiner* — Andrew Smyth
(74) *Attorney, Agent, or Firm* — Faegre Drinker Biddle & Reath LLP

(57) ABSTRACT

A system for determining a treatment plan in active ion beam treatment, to minimize unwanted dose, while maintaining or improving target dose coverage, whereby a beam is split into at least two sub-beams and where each sub-beam has a range shifter of different settings.

15 Claims, 6 Drawing Sheets

(56) References Cited

U.S. PATENT DOCUMENTS

| | | | | |
|---|---|---|---|---|
| 2011/0240874 | A1* | 10/2011 | Iwata | G21K 1/043 |
| | | | | 250/492.3 |
| 2014/0014851 | A1* | 1/2014 | Asaba | H05H 7/12 |
| | | | | 250/396 R |
| 2014/0031602 | A1* | 1/2014 | Fujimoto | A61N 5/1043 |
| | | | | 378/204 |
| 2014/0235919 | A1* | 8/2014 | Iwata | A61N 5/1043 |
| | | | | 600/1 |
| 2015/0352372 | A1* | 12/2015 | Takayanagi | A61N 5/1031 |
| | | | | 600/1 |
| 2017/0304650 | A1* | 10/2017 | Inaniwa | A61B 6/025 |
| 2017/0368371 | A1* | 12/2017 | Hanada | H05H 7/04 |

FOREIGN PATENT DOCUMENTS

| | | | | |
|---|---|---|---|---|
| EP | 2952225 A1 * | 12/2015 | | A61N 5/1043 |
| EP | 2952225 A4 * | 9/2016 | | A61N 5/1031 |
| EP | 2952225 B1 * | 6/2018 | | A61N 5/1077 |
| JP | 2004241190 A * | 8/2004 | | |
| JP | 2011-224342 A | 11/2011 | | |
| WO | WO-2014/045716 A1 | 3/2014 | | |

\* cited by examiner

SYSTEM AND METHOD FOR DETERMINING A TREATMENT PLAN FOR ACTIVE ION BEAM TREATMENT

This application is the National Stage of International Application No. PCT/EP2017/083736, filed Dec. 20, 2017, and claims benefit of European Patent Application No. 16205627.9, filed Dec. 21, 2016, the entire contents of which are incorporated by reference herein.

THE BACKGROUND OF THE INVENTION AND PRIOR ART

The present invention relates generally to solutions for minimizing unwanted dose in active ion beam radiation treatment of a target volume while maintaining or maximizing target dose coverage. More particularly, the invention relates to a system, and a corresponding method, for determining a treatment plan for active ion beam treatment, such that both unwanted dose minimization and maintained or maximized target dose coverage is obtained. The invention also relates to a computer program and a processor-readable medium.

Radiation treatment typically involves subjecting a target, such as a tumour within a patient, to one or more radiation beams. Ideally, a specific dose should be delivered to the target and minimal radiation should reach the surrounding tissue. In particular, the radiation to critical tissues or organs, such as the heart, brain and bladder, should be minimized, whereby the maximum and minimum doses for various tissues and organs are specified in a set of clinical goals. To verify a calculated radiation dose, the one or more radiation beams may instead be subjected to a verification phantom, in which the delivered dose can be measured.

In the field of radiation therapy treatment planning, treatment planners usually generate a radiation treatment plan, also referred to as a treatment plan, after having knowledge of the to-be-treated target volume in a patient's body by obtaining images of the target volume and surrounding regions, using for example a computer tomography (CT) scanner. The target volume is usually an organ in the patient's body that is affected by a tumour, for example a cancer.

In active scanning ion beam therapy, the ions are delivered in modulated pencil beams, also referred to as spots, grouped in several energy layers within a certain range of treatment energies supported by the machine. The energy limits of the machine will limit the ion range in the beam direction. The upper limit is in most cases sufficiently high to cover the most distal part of the target, while the low energy limit is sometimes too high, which could result in a situation of not being able to cover superficial targets. To be able to cover targets with parts close to the patient surface, range shifters of water-equivalent materials and different thicknesses are used. The range shifters will directly decrease the range of the ions, which is desired. However, a side-effect of the use of range shifters is that the pencil beam size, also referred to as spot size, increases and the lateral penumbra gets worse.

The use of inadequate planning methods often leads to inadequate radiation therapy treatment plans, which in turn leads to poor target dose coverage and/or unwanted dose distribution reaching the surrounding tissue and organs. In worst case, this may lead to the target volume not receiving the required treatment dose and/or damage to critical tissues or organs, such as the heart, the brain etc.

The inventor has therefore found that, in ion beam radiation treatment of a target volume, there is a need for minimizing dose to organs-at-risk (OAR), while maintaining or improving target coverage.

There is further a need for improved parameter generation and generation of a radiation therapy treatment plan without making it more complex or time-consuming for the planner, to allow both more and less experienced planners to produce improved plans, within reasonable time frames.

SUMMARY OF THE INVENTION

The object of the present invention is therefore to offer a solution for improving or optimizing upon existing parameter generation and radiation treatment plans to minimize unwanted dose, e.g. dose to organs at risk, while maintaining or improving target coverage.

This object is met by a system according to any of the claims 1-7, and a method according to any of the claims 8-12.

According to a further aspect of the invention the object is achieved by a computer program load able into the memory of at least one processor, and includes software adapted to implement the method proposed above when said program is run on at least one processor.

According to another aspect of the invention the object is achieved by a processor-readable medium, having a program recorded thereon, where the program is to control at least one processor to perform the method proposed above when the program is loaded into the at least one processor.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED EMBODIMENTS OF THE INVENTION

The aim of the embodiments presented herein is to overcome the defined problems by providing a system for determining a treatment plan in active ion beam treatment, to minimize unwanted dose, while maintaining or improving target dose coverage. Embodiments presented herein further aim at attaining improved parameter generation and generation of a radiation therapy treatment plan without making it more complex or time-consuming for the planner, to allow both more and less experienced planners to produce improved plans, within reasonable time frames.

In active scanning ion beam therapy, the ions are delivered by modulated pencil beams (spots) within a certain range of treatment energies, supported by the machine. As explained above, the energy limits of the machine will limit the ion range in the beam direction. The upper limit is in most cases sufficiently high to cover the most distal part of the target, while the low energy limit could result in a situation of not being able to cover superficial targets. To be able to cover targets with parts close to the patient surface, range shifters of water-equivalent materials and different thicknesses are used. The range shifters will directly decrease the range of the ions, which is desired. However, a side-effect of the use of range shifters is that the pencil beam size/spot size increases and the lateral penumbra gets worse.

Prior solutions include manually selecting a range shifter for each ion/radiation beam to be delivered. The inventor has realized that, in order to not degrade the full beam, it is desirable to be able to just use the range shifter for the part of the target that requires a range shifter. This gives higher planning and treatment precision, and achieves the aims of reducing the problem of increased pencil beam size/spot size, i.e. a worsened lateral penumbra, thereby minimizing unwanted dose, e.g. to organs at risk, while at the same time maintaining or improving target coverage.

Embodiment solutions based on this realization are now presented in more detail, in connection with the figures.

Figure 1:
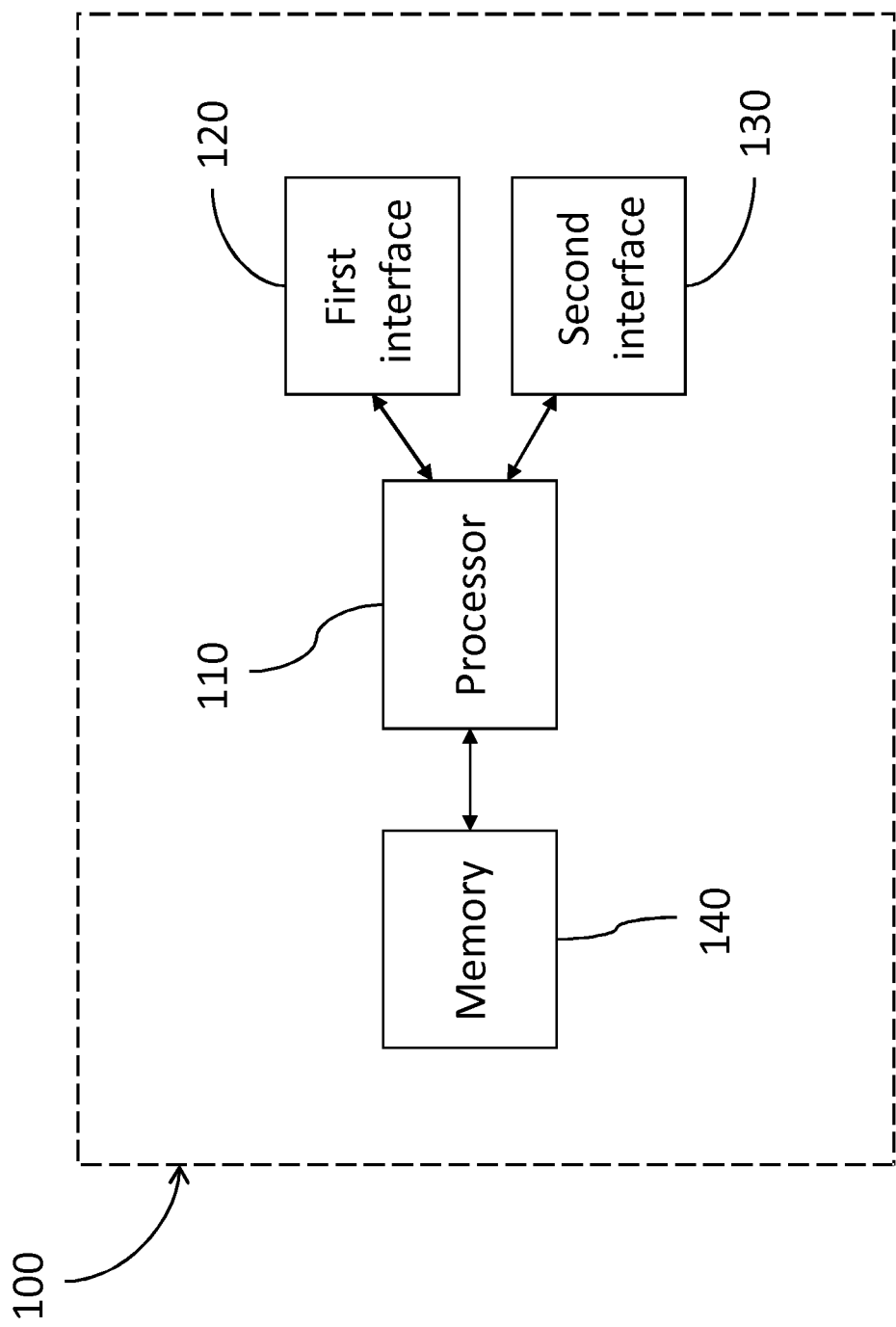
FIG. 1 shows an overview of a system according to one embodiment of the invention.

FIG. 1 shows an overview of a system 100 for determining a treatment plan in active ion beam treatment, to minimize unwanted dose, while maintaining or improving target dose coverage, according to one embodiment of the invention.

The system 100 includes a data processor 110 and a memory 140, said memory containing instructions executable by said data processor 110. In other words, the memory 140 is configured to store software for executing the below-described procedure when the software is being run on the processor 110. The system 100 may further comprise a first and at least a second interface, 120 and 130, respectively. For presentation purposes, FIG. 1 illustrates the interfaces 120 and 130 as separate entities. However, in a practical implementation, two or more of the interfaces may be integrated into a common unit.

The ion beam treatment technique used is an active scanning technique. Some non-limiting examples of active scanning techniques, for which the systems and methods presented herein may advantageously be used, are step-and-shoot scanning, line scanning and raster scanning (also referred to as quasi-discrete scanning).

The first interface 120 is configured to output image data for presentation on a graphical display. In some embodiments, the first interface 120 is configured to output graphical data corresponding to a graphical user interface (GUI) on a graphical display. The GUI may present information and selectable options by which a planner can provide input to the system and methods described herein for splitting the beam into a set of at least two sub-beams and/or optimizing one or more set of sub-beams in manners further described herein. The graphical data is output in response to control instructions from the processor 110.

The data processor 110 is configured to, for each of at least one delivery direction: define a beam; split said beam into at least two sub-beams and define a set of sub-beams, comprising said at least two sub-beams; associate a first sub-beam, from the set of at least two sub-beams, with a first range shifter setting; and associate a second sub-beam, from the set of at least two sub-beams, with a second range shifter setting, different from the first range shifter setting. Thereby, there is obtained a set of sub-beams having identical beam properties, except for a range shifter setting of each sub-beam which is unique for each sub-beam in the set. Beam properties in the context of this disclosure may comprise, but are not limited to, a selection of the following: an isocenter, a gantry angle, a couch angle and a snout at a specified position.

The data processor 110 is further configured to optimize the defined at least one set of sub-beams to determine a treatment plan.

Optimization is performed based on one or more optimization objectives. Examples of optimization objectives are uniform dose, minimum dose, and maximum dose objectives. One exemplary type of optimization is Single Field Optimization (SFO), where at least one of the beams (herein corresponding to sets of sub-beams) in the treatment plan has its own unique optimization objective. According to embodiments described herein, the SFO approach is further possible to apply on sub-beam level, for individual sub-beams, as well as to the set of sub-beams. A common application of SFO is Single Field Uniform Dose (SFUD), where each beam has its own uniform dose objective. SFUD optimization is commonly used to obtain plans which are robust against patient setup errors and range uncertainties.

In one or more embodiments, the data processor 110 is configured to, as a part of optimizing the at least one set of sub-beams to determine a treatment plan, optimize at least one set of sub-beams based on an optimization objective unique to that set of sub-beams.

In one or more embodiments, the data processor 110 is configured to, as a part of optimizing the at least one set of sub-beams to determine a treatment plan, optimize at least one sub-beam in a set of sub-beams based on an optimization objective unique to that sub-beam within that set of sub-beams.

In different embodiments, further described in connection with FIGS. 4a to 4c, the data processor 110 may be configured to optimize a selection of:

none, one or more sub-beams in each set of sub-beams that are to be comprised in a treatment plan based on an optimization objective unique to each of said none, one or more sub-beams within that set of sub-beams, if there is such an optimization objective;

none, one or more set of sub-beams, from all set of sub-beams that are to be comprised in a treatment plan, based on an optimization objective unique to that set of sub-beams, if there is such an optimization objective; and/or thirdly all sets of sub-beams that are to be comprised in a treatment plan using a common optimization objective, if there is such an optimization objective.

In this way, a large number of combinations with different levels of detail in the optimization step are enabled, whereby the optimization can include a combination of the different selections.

For example, in some cases it may be of importance for a user/planner to be able to adjust each sub-beam, or a selection of sub-beams in a set, separately, whereby the possibility to optimize on sub-beam level using a sub-beam specific optimization objective is advantageous, providing the highest possible level of detail and control of the dose delivery from each sub-beam. In other cases, it may be beneficial to be able to adjust a set of sub-beams separately, whereby the possibility to optimize on beam level (where a beam in the resulting plan is based on a set of sub-beams) using a beam-specific optimization objective. This gives a relatively high level of detail, being able to control the dose on the beam level, while the dose between the sub-beams is distributed freely. For example, this will be important when applying Single Field Optimization in general, and Single Field Uniform Dose optimization in particular, to obtain more robust treatment plans. In yet other cases, it may be beneficial to be able to adjust all sets of sub-beams that are to be comprised in a treatment plan (corresponding to all the beams of the resulting treatment plan) using a common optimization objective, thereby advantageously not having to perform identical adjustments separately for each set of sub-beams. Also, there will be more degrees of freedom in the optimization, possibly further reducing the unwanted dose to OARs, at the cost of less robust plans. This method could therefore benefit from being used in combination with robust optimization.

As described above, any combination of optimization on the three different levels (sub-beam, set of sub-beams, all sets of sub-beams) is possible, to provide the best possible treatment plan in each case.

In one or more embodiment, for each of the at least one delivery direction, the first range shifter setting indicates a first thickness of a range shifter of a first material having a particular density, and the second range shifter setting indicates a second thickness of a range shifter of the first or another material, wherein the thicknesses are defined in the delivery direction and the range shifters are intended to be placed upstream of the target volume. In the case where the second range shifter setting corresponds to no range shifter, this corresponds to the second thickness being zero.

In some embodiments, the memory 140 is configured to store a knowledge database, or predetermined input parameters. The memory 140 may further be configured to send input parameters from the stored knowledge database, or the stored predetermined input parameters, to the data processor 110, possibly in response to a control signal from the data processor 110. Correspondingly, the data processor 110 is in these embodiments configured to send a control signal and/or to receive input parameters from the memory 140.

In some embodiments, a second interface 130 is configured to forward one or more input parameters to the data processor 110. The data processor 110 is in these embodiments configured to receive input parameters from the second interface 130. The input parameters are in these embodiments preferably generated in response to user commands entered via an input device, for example a keyboard and/or computer mouse or other pointing device, joystick, touchscreen or any other suitable input device. The input may be provided via a GUI presented on a display by the first interface 120. In an embodiment, the at least one second interface 130 is configured to forward an input parameter to the data processor 110 in response to at least one input user command input via said GUI; wherein the data processor 110 is further configured to receive the input parameter and perform the step of splitting said beam into a set of at least two sub-beams in response to the received input parameter. In other words, the user is enabled to activate a "beam splitting" option by interacting with, or making a selection using, the GUI. In alternative embodiments, the data processor 110 may be configured to perform beam splitting, automatically: on all beams; on one or more specified beam in response to user input activating the beam splitting option as described above; or on one or more specified beam in response to fulfillment of a predetermined criterion or received activation signal.

Method embodiments for determining a treatment plan in ion beam treatment are described with reference to the flow diagram in FIGS. 2 and 4.

Figure 2:
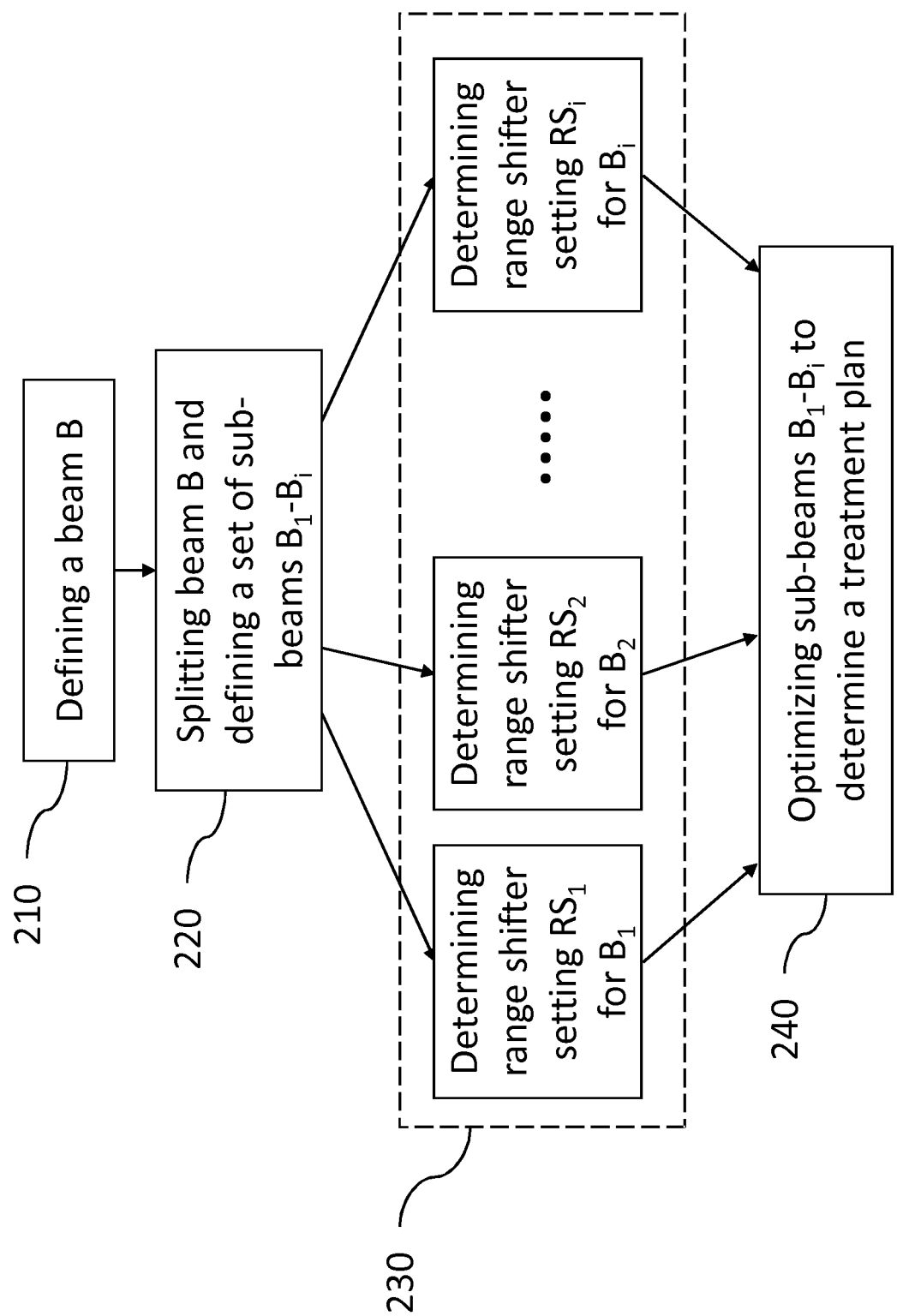
FIG. 2 shows a flow diagram illustrating embodiments of the proposed method.

FIG. 2 shows a flow diagram of a method according to one embodiment of the invention. The method of FIG. 2 comprises, for each of at least one delivery direction:

In step 210: defining a beam.

A beam defined in step 210 may hereinafter be referred to as B.

Step 210 of defining a beam may comprise defining any or all of an isocenter, a gantry angle, and a couch angle.

In step 220: splitting said beam into at least two sub-beams and defining a set of sub-beams, comprising said at least two sub-beams.

This may hereinafter be referred to as splitting said beam B into at least two sub-beams $B_1$ and $B_2$ and defining a set $B_1$-$B_i$ of sub-beams, comprising said at least two sub-beams $B_1$ and $B_2$.

Splitting the beam B, in the context of the present disclosure, comprises generating a set $B_1$-$B_i$ of at least two sub-beams $B_1$ and $B_2$, based on the defined beam B, wherein each sub-beam $B_1$-$B_i$ inherits at least the following beam properties from the beam B: an isocenter, a gantry angle, a couch angle and in some cases a snout at a specified position In step 230: associating a first sub-beam $B_1$, from the set $B_1$-$B_i$ of at least two sub-beams, with a first range shifter setting, and associating a second sub-beam $B_2$, from the set $B_1$-$B_i$ of at least two sub-beams, with a second range shifter setting, different from the first range shifter setting.

The first and second range shifter settings may, respectively, be set automatically by the system, or may be set based on user input indicating a range shifter setting selection.

Thereby, there is obtained a set of sub-beams having identical properties, except for a range shifter setting which is unique for each sub-beam. The identical properties include, but are not limited to, the isocenter, the gantry angle, and the couch angle. The similarities are advantageous, as the set of sub-beams may be treated as a single beam, by a user or by a system or apparatus performing the method according to embodiment presented herein, thereby enabling subjecting the beam (i.e. the set of sub-beams) to common processing, adjustments etc. This also enables a treatment planner to generate parameter settings and a treatment plan easier and faster, as the planner will not have to make separate identical adjustments or settings for several sub-beams, but instead performs the adjustments or settings once to simultaneously process all sub-beams within the set of sub-beams. As is evident to a person skilled in the art, other types of processing that are also identical for all sub-beams comprised in a set of sub-beams, may advantageously be performed once, i.e. simultaneously, for all the sub-beams in the set.

At the same time, the sub-beams in a set of sub-beams may be treated and processed separately in relation to their range shifter settings, which gives the advantage of not degrading the full beam when it is desirable to be able to just use the range shifter, or range shifters, for the part, or parts, of the target that requires a range shifter. This in turn gives higher planning and treatment precision, and achieves the aims of reducing unwanted dose to surrounding tissue, or organs at risk, while maintaining or maximizing target coverage.

Figure 3A:
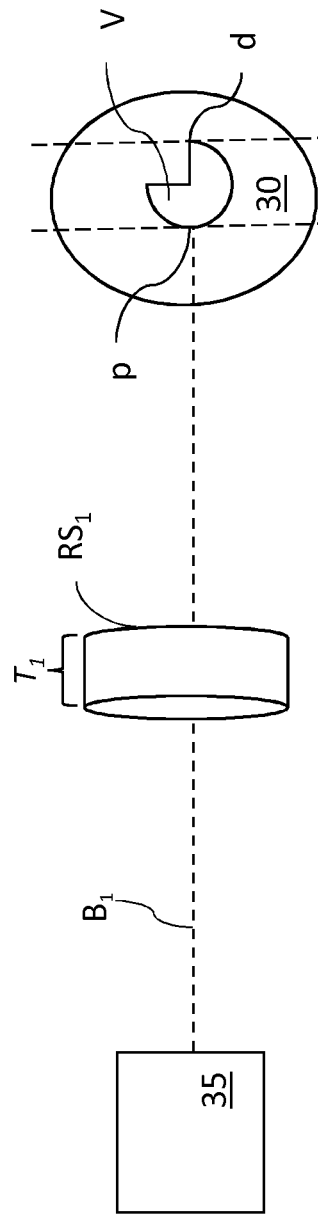
FIGS. 3A-C show overviews of an ion beam therapy system using parameter settings according to embodiments of the invention.
Figure 3B:
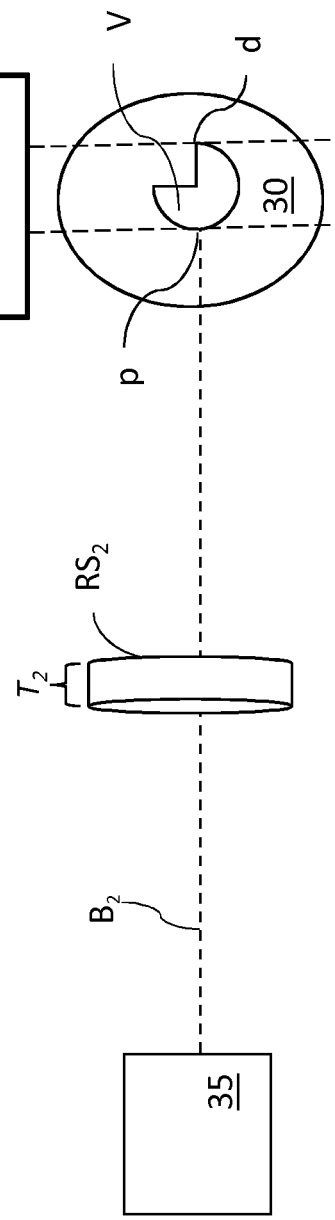
Figure 3C:
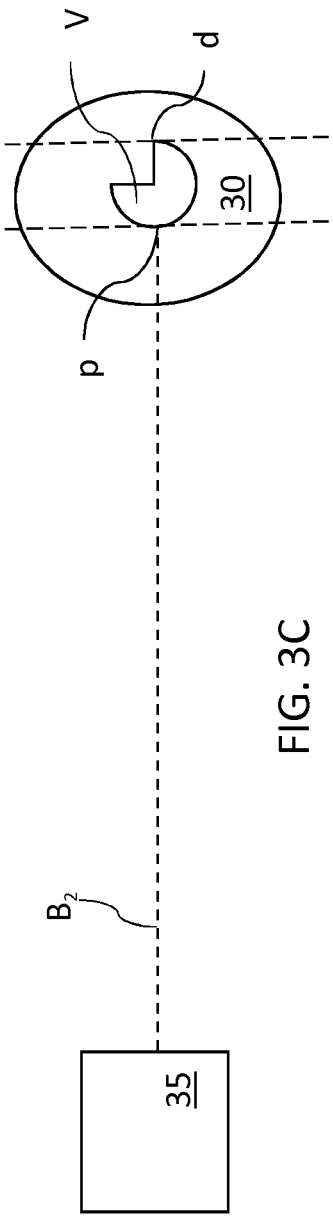

FIGS. 3a to 3c show overviews of an ion beam therapy system using parameter settings according to one or more embodiment.

For simplicity, only two sub-beams $B_1$, $B_2$ ($B_1$-$B_i$, where i=2) are shown in FIGS. 3a to 3c, but, as understood by the skilled person, a set of sub-beams $B_1$-$B_i$ could comprise any suitable number of sub-beams. Step 230 would then comprise, in an iterative manner for each of the sub-beams in the set $B_1$-$B_i$, associating sub-beam $B_i$ with a range shifter setting $RS_i$, wherein each range shifter setting $RS_1$, $RS_2$, ..., $RS_i$ is different from the other range shifter settings assigned to the sub-beams in the set $B_1$-$B_i$, respectively. In other words, each sub-beam in the set $B_1$-$B_i$ is assigned a unique range shifter setting.

Below, the embodiments are, again only for illustrational purposes, described relating to a set of only two sub-beams $B_1$, $B_2$ ($B_1$-$B_i$, where i=2), but they could be applied on a set of any suitable number of sub-beams.

In all embodiments presented herein, for each of the at least one delivery direction, the first range shifter setting indicates a first (water-equivalent) thickness $T_1$ of a selected first range shifter $RS_1$ of a first material having a particular density, and the second range shifter setting indicates a second (water-equivalent) thickness $T_2$ of a selected second range shifter $RS_2$ of the first or another material, wherein $T_1 \neq T_2$. In the same manner, for a set $B_1$-$B_i$ of sub-beams, each unique range shifter setting $RS_1$, $RS_2$, ..., $RS_i$ indicates a respective unique thickness $T_1$, $T_2$, ..., $T_i$, i.e different from the other thicknesses, indicated by the other range shifter setting, assigned to the sub-beams in the set. The thicknesses are defined in the delivery direction of the beam B and the range shifters $RS_1$, $RS_2$ are intended to be placed upstream of a target volume V, when used in a system for radiation treatment of the target volume V, as schematically illustrated in FIGS. 3a to 3c. The target volume V has a most proximal point p, located on the proximal edge of the volume V, and a most distal point d, located on the distal edge of the target volume V.

The range shifter settings are selected such that unwanted dose is minimized, while target dose coverage is maintained or improved.

In one or more embodiments, the second range shifter setting corresponds to no range shifter. In other words, in this one or more embodiment, the defined thickness $T_2$ of the second range shifter $RS_2$ is zero, whereby no range shifter will be used in conjunction with the second sub-beam $B_2$ when used in a system for radiation treatment of the target volume V. This embodiment is shown in FIG. 3c. In this case, the selection of no range shifter (range shifter with thickness $T_2$=0) is the selection that best achieves minimization of unwanted dose, while maintaining or improving target dose coverage.

A patient 30 that is to be subjected to ion beam therapy is shown schematically to the right in FIGS. 3a, 3b and 3c. A target volume V within the patient 30 represents the organ or other tissue that is to receive the radiotherapy. As is common in the art, there may also be defined critical regions within the patient 30 referred to as organs at risk, which are regions in which it is particularly important to avoid, or at least minimize, radiation. Such areas are not shown in FIGS. 3a, 3b and 3c. As exemplified in the Figures, a radiation source 35 provides an ion beam, which may be a sub-beam, having a sufficient energy to achieve the desired maximum range, or radiological (water equivalent) depth of interest, i.e. reaching to the most distal point d, on the distal edge, of the target volume V.

The target volume V typically has an irregular shape so that the water equivalent distance to the distal edge will vary over the target. For example, in FIGS. 3a, 3b and 3c, the lower portion of the target V extends further into the patient's body than the upper portion. The patient geometry will also affect the (water-equivalent) distance to the target. For calculating the water-equivalent distance the beam has to travel inside the body, the traversed geometrical distances in different body materials are translated to water-equivalent thicknesses. Soft body tissues, such as adipose and fat, have material properties close to water and the water-equivalent distances will be close to the geometrical distances, whereas bone or air pockets will show larger differences between geometrical and water-equivalent distances. A bone region in the beam path will for example increase the water equivalent depth, while an air cavity will reduce it, as compared to the geometrical distance.

The maximum beam energy is determined such that the maximum ion beam range agrees with the most distal point d on the target, and the minimum beam energy is determined such that the minimum ion beam range agrees with the most proximal point p on the target.

In alternative embodiments, a maximum beam energy/maximum radiological depth may be determined automatically, based on the available energy levels; or a maximum beam energy/maximum radiological depth may be determined in response to user input indicating selection of a maximum beam energy/maximum radiological depth for a sub-beam intended for use with a range shifter. Optionally, a sub-beam intended for use with no range shifter could have a minimum radiological depth specified. The minimum beam energy/minimum radiological depth may be determined automatically, based on the available energy levels; or a minimum beam energy/minimum radiological depth may be determined in response to user input indicating selection of a minimum beam energy/minimum radiological depth. Automatic system determination of maximum and/or minimum radiological depths is advantageous as it improves usability of the system by making it easier for a user. Determination of maximum and/or minimum radiological depths in response to user input is advantageous as it enables a more precise control of settings by the user.

In one or more embodiment, the data processor 110 may be configured to automatically determine a maximum beam energy/maximum radiological depth based on the available energy levels. In another embodiment, the data processor 110 may be configured to determine a maximum beam energy/maximum radiological depth based on user input, the user input indicating selection of a maximum beam energy/maximum radiological depth for a sub-beam intended for use with a range shifter.

In one or more embodiment, the data processor 110 may be configured to automatically determine a minimum beam energy/minimum radiological depth based on the available energy levels. In another embodiment, the data processor 110 may be configured to determine a minimum beam energy/minimum radiological depth based on user input, the user input indicating selection of a minimum beam energy/minimum radiological depth.

In cases where the minimum beam energy is too high to be able to cover the most proximal point p on the target, the use of range shifters is introduced.

According to embodiments described herein, the at least two sub-beams in a defined set have the same properties, except for their range shifter settings. Therefore, when used in a system for ion beam therapy of a target volume, beams, corresponding to the sub-beams in a set of sub-beams, will be delivered from the same beam direction but using different range shifters, meaning that different radiological depths are reached from the same beam direction. This enables the delivered radiation to be controlled as precisely as possible, to avoid unnecessary radiation to parts of the patient outside of the target V. Thereby, the dose will conform to different parts of the target, providing a reduced lateral penumbra, while maintaining or improving target coverage.

The method of FIG. 2 further comprises:

In step 240: optimizing the at least one set of sub-beams to determine a treatment plan.

Figure 4A:
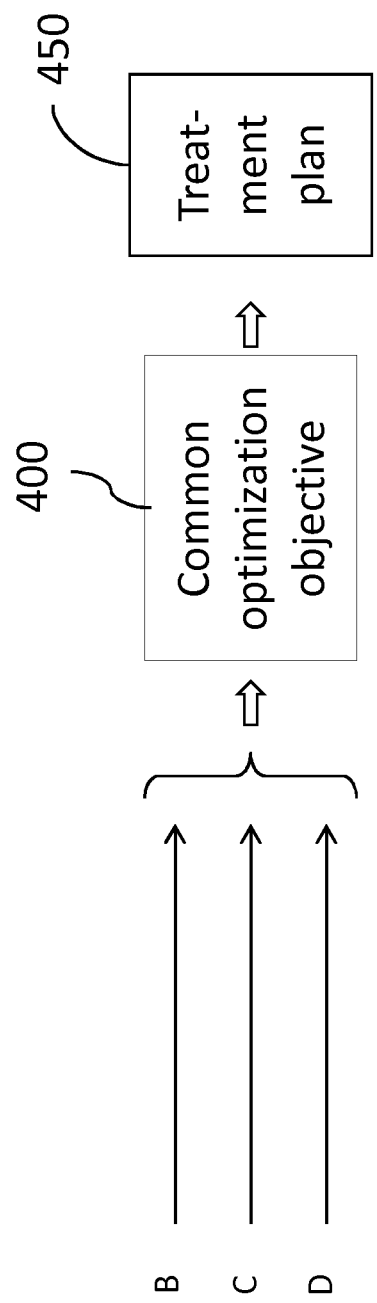
FIGS. 4A-C show illustrating embodiments of generation of treatment plans.
Figure 4B:
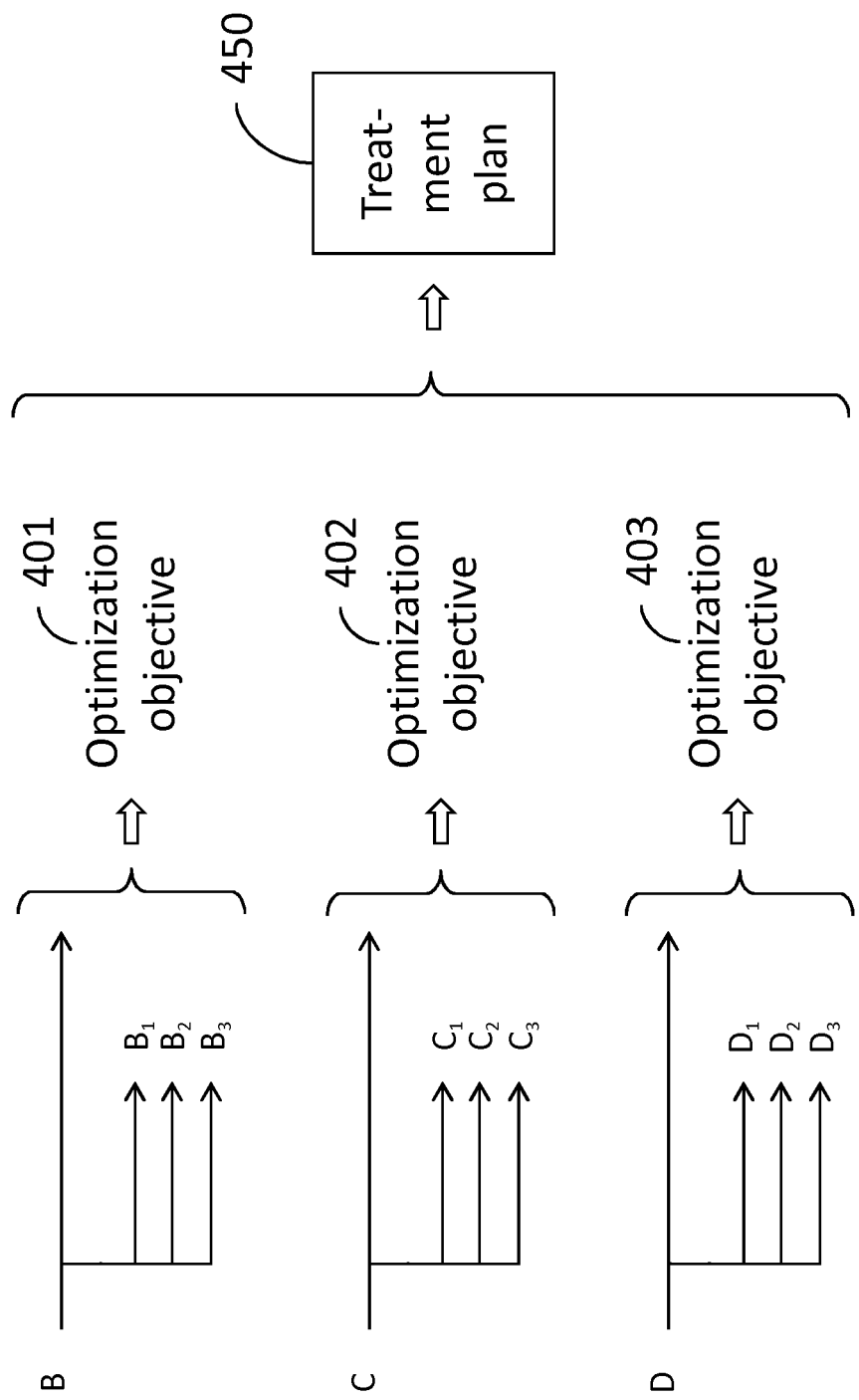
Figure 4C:
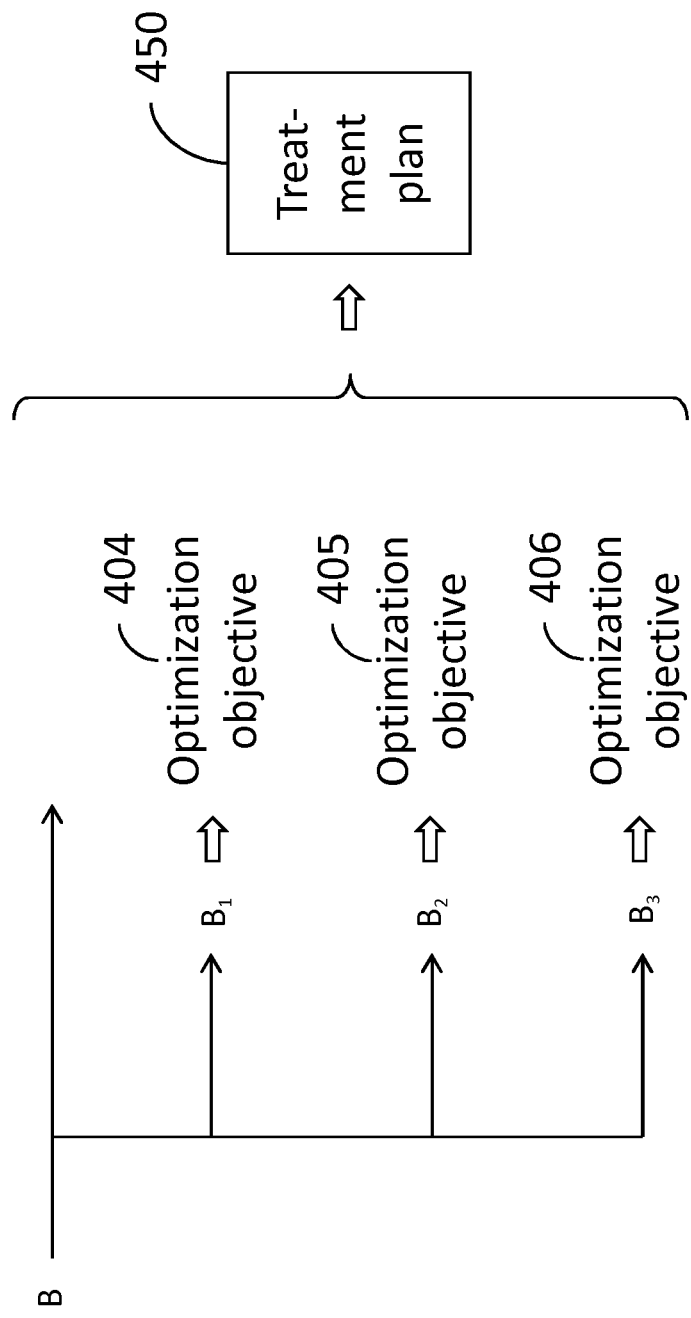

FIGS. 4a to 4c show illustrating optimization embodiments, leading to determination of a treatment plan 450.

As illustrated in FIG. 4a, step 240 may, in one or more embodiments, comprise optimizing all sets B, C, D of sub-beams (which may also be referred to as beams B, C, D) that are to be comprised in a treatment plan 450 using a common optimization objective 400.

As illustrated in FIG. 4b, step 240 may, in one or more embodiments, comprise optimizing at least one set B, C, D of sub-beams based on an optimization objective 401, 402, 403 unique to that set of sub-beams, i.e. to the set B, C, D, respectively.

As illustrated in FIG. 4c, step 240 may, in one or more embodiments, comprise optimizing at least one sub-beam $B_1$, $B_2$, $B_3$, in a set B of sub-beams, based on an optimization objective 404, 405, 406 unique to that sub-beam $B_1$, $B_2$, $B_3$ within that set B of sub-beams.

In one or more embodiments, optimizing the at least one set of sub-beams to determine a treatment plan in step 240 may comprise a combination of the embodiments presented in connection with FIGS. 4a to 4c, e.g. by the method step 240 comprising:

optimizing none, one or more sub-beams in each set of sub-beams that are to be comprised in a treatment plan based on an optimization objective unique to each of said none, one or more sub-beams within that set of sub-beams, if there is such an optimization objective;

optimizing none, one or more set of sub-beams, from all set of sub-beams that are to be comprised in a treatment plan, based on an optimization objective unique to that set of sub-beams, if there is such an optimization objective; and optimizing all sets of sub-beams that are to be comprised in a treatment plan using a common optimization objective, if there is such an optimization objective.

Thereby, a large number of combinations with different levels of detail in the optimization step are enabled. Hence, there are many different ways to arrive at an improved treatment plan using embodiments presented herein, either automatically selected by the system or selected based on user input.

In one or more embodiments, a treatment plan according to any embodiment presented herein may be in DICOM format.

In any of the method embodiments presented herein, the step of splitting the defined beam into a set of sub-beams may be done in response to a received input parameter. The method may in these cases further comprise receiving an input parameter, and performing the step of splitting a beam into a set of at least two sub-beams in response to the received input parameter. The input may be provided via a GUI presented on a display. In some embodiments, the user is enabled to generate an input parameter to activate the "beam splitting" option by interacting with, or making a selection using, the GUI.

In alternative embodiments, step 220 of splitting a beam B into a set $B_1$-$B_i$ of at least two sub-beams $B_1$ and $B_2$, comprises: automatically splitting all beams defined by the system 100 into a set $B_1$-$B_i$ of at least two sub-beams; splitting one or more defined beam into a set $B_1$-$B_i$ of at least two sub-beams in response to user input activating the beam splitting option, as described above; or splitting one or more defined beam into a set $B_1$-$B_i$ of at least two sub-beams in response to fulfillment of a predetermined criterion or in response to a received activation signal. Automatic beam splitting on all defined beams, or a selection of the defined beams, based on fulfillment of a predetermined criterion or in response to a received activation signal, is advantageous as it improved the usability of the system, thereby making it easier for the user. Splitting of one or more beams in response to user input is advantageous as it enables a more precise control of settings by the user.

Further Embodiments

An alternative way to achieve penumbra reduction, i.e. minimize unwanted dose, which could be used in combination with the embodiments presented herein to obtain even further improved lateral penumbrae and reduced side effects, is to use patient-specific aperture blocks also in active scanning.

All of the process steps, as well as any sub-sequence of steps, described with reference to FIGS. 2-4 above may be controlled by means of a programmed processor. Moreover, although the embodiments of the invention described above with reference to the drawings comprise processor and processes performed in at least one processor, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for determining a treatment plan in active ion beam treatment using an active spot-scanning technique, to minimize unwanted dose, while maintaining or improving target dose coverage of a target volume, comprising:
a data processor; and
a memory, said memory containing instructions executable by said data processor;
wherein the data processor is configured to, for each of at least one delivery direction:
define a first beam to be optimized and define a second beam to be optimized by the data processor of the system;
split said first beam by the data processor, without use of a range modulation wheel, into at least two sub-beams and define a first set of sub-beams, consisting of said at least two sub-beams of the first set of sub-beams, wherein each of the sub-beams of the first set of sub-beams inherits at least the following first beam properties from the first beam: an isocenter; a gantry angle; and a couch angle;
split said second beam by the data processor, without use of a range modulation wheel, into at least two sub-beams and define a second set of sub-beams, consisting of said at least two sub-beams of the second set of sub-beams, wherein each of the sub-beams of the second set of sub-beams inherits at least the following second beam properties from the second beam: an isocenter; a gantry angle; and a couch angle, the first beam properties different from the second beam properties;
associate a first sub-beam of the first set of sub-beams, from the set of al least two sub-beams of the first set of sub-beams, with a first range shifter setting;
associate a second sub-beam of the first set of sub-beams, from the set of at least two sub-beams of the first set of sub-beams, with a second range shifter setting, different from the first range shifter setting;
associate a first sub-beam of the second set of sub-beams, from the set of at least two sub-beams of the second set of sub-beams, with a third range shifter setting;
associate a second sub-beam of the second set of sub-beams, from the set of at least two sub-beams of the second set of sub-beams, with a fourth range shifter setting, different from the third range shifter setting; and
optimize the first set of sub-beams and the second set of sub-beams to determine the treatment plan.

2. The system of claim 1, wherein the second range shifter setting corresponds to no range shifter.

3. The system of claim 1, wherein, for each of the at least one delivery direction, the first range shifter setting indicates a first thickness of a range shifter of a first material having a particular density, and the second range shifter setting indicates a second thickness of a range shifter of the first or another material, wherein the thicknesses are defined in the delivery direction and the range shifters are intended to be placed upsteam of the target volume.

4. The system of claim 1, wherein the data processor is configured to, as a part of optimizing the first set of sub-beams and the second set of sub-beams to determine a treatment plan, optimize at least one set of sub-beams of each of the first set of sub-beams and the second set of sub-beams based on an optimization objective unique to the first set of sub-beams and the second set of sub-beams.

5. The system of claim 1, wherein the data processor is configured to, as a part of optimizing the first set of sub-beams and the second set of sub-beams to determine a treatment plan, optimize at least one sub-beam in the first set of sub-beams based on an optimization objective unique to that sub-beam within the first set of sub-beams and optimize at least one sub-beam in the second set of sub-beams based on an optimization objective unique to that sub-beam within the second set of sub-beams.

6. The system of claim 1, further comprising:
a first interface, configured to output graphical data corresponding to a graphical user interface on a graphical display;
at least one second interface, configured to forward an input parameter to the data processor in response to at least one input user command input via said GUI;
wherein the data processor is further configured to receive the input parameter and perform the step of splitting said beam into a set of at least two sub-beams in response to the received input parameter.

7. A method for determining a treatment plan in active ion beam treatment using an active spot-scanning technique, to minimize unwanted dose, while maintaining or improving target dose coverage of a target volume, the method comprising:
for each of at least one delivery direction:
defining, by at least one processor, a first beam to be optimized and defining a second beam to be optimized to determine the treatment plan;
splitting said first beam by the at least one processor, without use of a range modulation wheel, into at least two sub-beams and defining a first set of sub-beams, consisting of said at least two sub-beams of the first set of sub-beams, wherein each of the sub-beams of the first set of sub-beams inherits at least the following beam properties from the first beam: an isocenter; a gantry angle; and a couch angle;
splitting said second beam by the data processor, without use of a range modulation wheel, into at least two sub-beams and define a second set of sub-beams, consisting of said at least two sub-beams of the second set of sub-beams, wherein each of the sub-beams of the second set of sub-beams inherits at least the following second beam properties from the second beam: an isocenter; a gantry angle; and a couch angle, the first beam properties different from the second beam properties;
associating a first sub-beam of the first set of sub-beams, from the set of at least two sub-beams of the first set of sub-beams, with a first range shifter setting;
associating a second sub-beam of the first set of sub-beams, from the set of at least two sub-beams of the first set of sub-beams, with a second range shifter setting, different from the first range shifter setting;
associating a first sub-beam of the second set of sub-beams, from the set of at least two sub-beams of the second set of sub-beams, with a third range shifter setting;
associating a second sub-beam of the second set of sub-beams, from the set of at least two sub-beams of the second set of sub-beams, with a fourth range shifter setting, different from the third range shifter setting; and optimizing the first set of sub-beams and the second set of sub-beams to determine the treatment plan.

8. The method of claim 7, wherein the second range shifter setting corresponds to no range shifter.

9. The method of claim 7, wherein, for each of the at least one delivery direction, the first range shifter setting indicates a first thickness of a range shifter of a first material having a particular density, and the second range shifter setting indicates a second thickness of a range shifter of the first or another material, wherein the thicknesses are defined in the delivery direction and the range shifters are intended to be placed upstream of the target volume.

10. The method of claim 7, wherein the step of optimizing the first set of sub-beams and the second set of sub-beams to determine a treatment plan comprises optimizing at least one set of sub-beams of each of the first set of sub-beams and the second set of sub-beams based on an optimization objective unique to the first set of sub-beams and the second set of sub-beams.

11. The method of claim 7, wherein the step of optimizing the first set of sub-beams and the second set of sub-beams to determine a treatment plan comprises optimizing at least one sub-beam in the first set of sub-beams based on an optimization objective unique to that sub-beam within the set of sub-beams and optimizing at least one sub-beam in the second set of sub-beams based on an optimization objective unique to that sub-beam within the second set of sub-beams.

12. The method of claim 7, further comprising receiving an input parameter, wherein the step of splitting said beam into a set of sub-beams is done in response to the received input parameter.

13. The method according to claim 7, wherein the active spot-scanning technique is one of step-and-shoot scanning, line scanning, or raster scanning.

14. A non-transitory computer-readable medium storing a computer program, the computer program loadable into a memory of the at least one processor, the computer program comprising software for executing the method according to claim 7 when the computer program is run on the at least one processor.

15. A method for determining a treatment plan in active ion beam treatment using an active spot-scanning technique, to minimize unwanted dose, ile maintaining or improving target dose coverage of a target volume, the method comprising:
for each of at least one delivery direction:
defining, by at least one processor, a first beam to be optimized and defining a second beam to be optimized to determine the treatment plan;
splitting said first beam by the at least one processor, without use of a range modulation wheel, into at least two sub-beams and defining a first set of sub-beams, comprising said at least two sub-beams of the first set of sub-beams, wherein each of the sub-beams of the first set of sub-beams inherits at least the following beam properties from the first beam: an isocenter; a gantry angle; a couch angle; and a snout at a specified position;
splitting said second beam by the data processor, without use of a range modulation wheel, into at least two sub-beams and define a second set of sub-beams, comprising said at least two sub-beams of the second set of sub-beams, wherein each of the sub-beams of the second set of sub-beams inherits at least the following second beam properties from the second beam: an isocenter; a gantry angle; a couch angle; and a snout at a specified position, the first beam properties different from the second beam properties;
associating a first sub-beam of the first set of sub-beams, from the set of at least two sub-beams of the first set of sub-beams, with a first range shifter setting;
associating a second sub-beam of the first set of sub-beams, from the set of at least two sub-beams of the first set of sub-beams, with a second range shifter setting, different from the first range shifter setting;
associating a first sub-beam of the second set of sub-beams, from the set of at least two sub-beams of the second set of sub-beams, with a third range shifter setting;
associating a second sub-beam of the second set of sub-beams, from the set of at least two sub-beams of the second set of sub-beams, with a fourth range shifter setting, different from the third range shifter setting; and
optimizing the first set of sub-beams and the second set of sub-beams to determine the treatment plan.

\* \* \* \* \*